United States Patent
Lee et al.

(10) Patent No.: US 11,298,428 B2
(45) Date of Patent: *Apr. 12, 2022

(54) NANOCARRIER FOR SELECTIVE FLUORESCENCE LABELING OF CANCER CELL AND PREPARATION METHOD THEREFOR

(71) Applicant: SEOUL NATIONAL UNIVERSITY R&DB FOUNDATION, Seoul (KR)

(72) Inventors: Kang Won Lee, Suwon-si (KR); Yoon Jeong, Suwon-si (KR); Sara Lee, Suwon-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 35 days.

This patent is subject to a terminal disclaimer.

(21) Appl. No.: 16/462,098

(22) PCT Filed: Feb. 20, 2017

(86) PCT No.: PCT/KR2017/001829
§ 371 (c)(1),
(2) Date: May 17, 2019

(87) PCT Pub. No.: WO2018/092984
PCT Pub. Date: May 24, 2018

(65) Prior Publication Data
US 2020/0268903 A1 Aug. 27, 2020

(30) Foreign Application Priority Data

Nov. 18, 2016 (KR) .................. 10-2016-0154441

(51) Int. Cl.
*A61K 47/69* (2017.01)
*A61K 49/00* (2006.01)
*A61K 47/55* (2017.01)

(52) U.S. Cl.
CPC ........ *A61K 47/6907* (2017.08); *A61K 47/551* (2017.08); *A61K 49/0036* (2013.01); *A61K 49/0082* (2013.01)

(58) Field of Classification Search
None
See application file for complete search history.

(56) References Cited

U.S. PATENT DOCUMENTS

| 9,241,921 | B2 | 1/2016 | Modi |
| 2010/0331819 | A1 | 12/2010 | Hossainy et al. |
| 2011/0201695 | A1 | 8/2011 | Mourier-Robert et al. |
| 2012/0283328 | A1 | 11/2012 | Modi |
| 2020/0384128 | A1 | 12/2020 | Lee et al. |

FOREIGN PATENT DOCUMENTS

| CN | 109562193 | A | 4/2019 |
| EP | 3479846 | A1 | 5/2019 |
| JP | 2002-512942 | A | 5/2002 |
| KR | 1019980014197 | A | 5/1998 |
| KR | 10-0852944 | B1 | 8/2008 |
| KR | 2012-0098191 | A | 9/2012 |
| WO | 98/23293 | A1 | 6/1998 |
| WO | 99/55230 | A1 | 11/1999 |

OTHER PUBLICATIONS

Guo et al. Dual-functional alginic acid hybrid nanospheres for cell imaging and drug delivery. 2009 Small 5: 709-717. (Year: 2009).*
Kong et al. Design and investigation of nanoemulsified carrier based on amphiphile-modified hyaluronic acid. 2011 Carbohydr. Polym. 83: 462-469. (Year: 2011).*
Extended European Search Report dated Jul. 7, 2020 in European Patent Application No. 17871175.0 filed Feb. 20, 2017, 12 pages.
Kong, M., et al., "Investigations on skin permeation of hyaluronic acid based nanoemulsion as transdermal carrier", Carbohydrate Polymers, vol. 86, Issue 2, Aug. 15, 2011, pp. 837-843, https://doi.org/10.1016/j.carbpol.2011.05.027.
Notice of Reasons for Refusal dated Jun. 23, 2020 in Japanese Patent Application No. 2019-526463 filed Feb. 20, 2017, 10 pages.
Zhang, L.W., et al. "Oil components modulate the skin delivery of 5-aminolevulinic acid and its ester prodrug from oil-in-water and water-in-oil nanoemulsions." International journal of nanomedicine, vol. 6, Apr. 5, 2011, pp. 693-704. DOI:10.2147/IJN.S17524.
International Search Report for PCT/KR2017/001829 dated Aug. 16, 2017, all pages.
Written Opinion for PCT/KR2017/001829 dated Aug. 16, 2017, all pages.
Luciana Mattoso Pires de Campos Araùjo, et al., "Development of microemulsions to topically deliver 5-aminolevulinic acid in photodynamic therapy," European Journal of Pharmaceutics and Biopharmaceutics 75 (2010) 48-55.
M. Porra, et al., "Properties of water-in-oil (W/O) nano-emulsions prepared by a low-energy emulsification method," Colloids and Surfaces A: Physicochemical and Engineering Aspects 324 (2008) 181-188.
Jianting Wang, et al., "Folate mediated self-assembled phytosterol-alginate nanoparticles for targeted intracellular anticancer drug delivery," Colloids and Surfaces B: Biointerfaces 129 (2015) 63-70.
Shu-Jyuan Yang, et al., "Alginate-folic acid-modified chitosan nanoparticles for photodynamic detection of intestinal neoplasms," Biomaterials 32 (2011) 2174-2182.
Yoon Jeong, et al., "Selective Uptake by Cancer Cells based on 5-Aminolevulinic Acid (5-ALA) for Fluorescence Image Guided Surgery," SOC-12, 20th Anniversary International Symposium of the KSBM 2016, Sep. 29-30, 2016, KIST, Seoul, Korea, 1 page.

(Continued)

*Primary Examiner* — Jennifer Lamberski
(74) *Attorney, Agent, or Firm* — Kilpatrick Townsend & Stockton LLP

(57) ABSTRACT

An embodiment of the present invention provides a nanocarrier in a micelle structure, a pharmaceutical composition for diagnosis of cancer, comprising the same nanocarrier, and a method for preparing the same nanocarrier. The nanocarrier is obtained by dispersing a water-in-oil nanoemulsion containing an oil phase ingredient, a surfactant, and an aqueous phase ingredient inclusive of a cancer cell fluorescence-inducing substance and a cancer cell-targeting polysaccharide in water to remove the oil phase ingredient, whereby the nanocarrier includes the aqueous phase ingredient.

16 Claims, 14 Drawing Sheets

(56) References Cited

OTHER PUBLICATIONS

Kangwon Lee, "Biomedical Imaging Applications of Fluorescence-based Nanotechnology," 2016 Annual Fall Meeting of The Korean BioChip Society, 1 page.

Hyukjin Lee, et al., "Target-specific intracellular delivery of siRNA using degradable hyaluronic acid nanogels," Journal of Controlled Release 119 (2007) 245-252.

Eun Ji Hong, et al., "Targeted and effective photodynamic therapy for cancer using functionalized nanomaterials," Acta Pharmaceutica Sinica B 2016;6(4):297-307.

Ramesh Subbiah, "Development of Contrast Agents for The Selective Labeling for Cancerous Lesions using A Hydrogel-based Nanoemulsions," The Polymer Society of Korea, 2016.4, 53-53.

Xing Ma, et al., "Targeted Delivery of 5-Aminolevulinic Acid by Multifunctional Hollow Mesoporous Silica Nanoparticles for Photodynamic Skin Cancer Therapy," ACS Applied Materials & Interfaces 2015, 7, 10671-10676.

Haijie Han, et al., "Intracellular Dual Fluorescent Lightup Bioprobes for Image-Guided Photodynamic Cancer Therapy," Small Journal 2016, 12, No. 28, 3870-3878.

Notification of reason for refusal dated Oct. 12, 2017 in Korean Patent Application No. 10-2016-0154441, filed Nov. 18, 2016, 9 pages.

Decision to Grant dated Aug. 13, 2018 in Korean Patent Application No. 10-2016-0154441, filed Nov. 18, 2016, 3 pages.

Notification of reason for refusal dated Jun. 5, 2018 in Korean Patent Application No. 10-2016-0154441, filed Nov. 18, 2016, 9 pages.

Shu-Jyuan Yang et al., "Alginate-folic acid-modified chitosan nanoparticles for photodynamic detection of intestinal neoplasms," Biomaterials 32 (2011) 2174-2182, www.eisevier.com/locate/biomaterials.

Li-Wen Zhang et al., "Oil components modulate the skin delivery of 5-aminolevulinic acid and its ester prodrug from oil-in-water and water-in-oil nanoemulsions," International Journal of Nanomedicine 2011:6 693-704, www.dovepress.com DOI:10.2147/IJN.S17524.

Office action for Chinese Patent Appln No. 201780071743.X dated Jun. 8, 2021, all pages.

Notice of Reasons for Refusal for Japanese Patent Appln No. 2019-52643 dated Mar. 30, 2021, all pages.

\* cited by examiner

FIG. 2
(A)
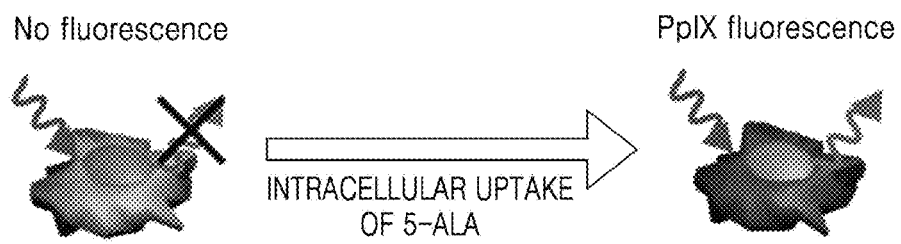
(B)
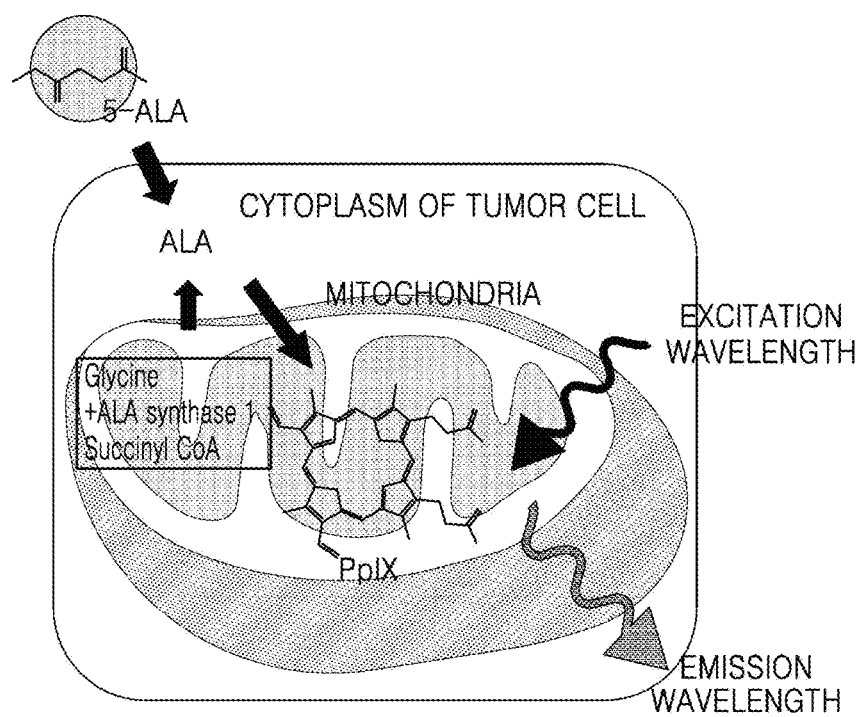

NANOCARRIER FOR SELECTIVE FLUORESCENCE LABELING OF CANCER CELL AND PREPARATION METHOD THEREFOR

TECHNICAL FIELD

The present disclosure relates to a nanocarrier for selective fluorescence labeling of cancer cells, and a method of preparing the same. More particularly, the present disclosure relates to a nanocarrier including a cancer cell fluorescence-inducing substance that is absorbed by cancer cells in vivo to produce a fluorescent substance and a cancer cell-targeting polysaccharide that selectively binds to cancer cells, and a method of preparing the same.

BACKGROUND ART

5-Aminolevulinic acid (5-ALA) has been used as a fluorescent substance for tumor surgery since 1979, and is a substance having few side effects when used clinically. When taken by a patient, 5-ALA is known to produce protoporphyrin IX (PpIX) by reacting with the patient's glioma cells. 5-ALA is converted into PpIX which is an intermediate in the heme biosynthesis pathway within mitochondria. 5-ALA in itself has no fluorescent properties, but PpIX produced by reacting 5-ALA with cancer cells emits fluorescence of 635 nm at an excitation wavelength of about 400 nm to distinguish malignant glioma from normal tissues. The previous studies reported that use of 5-ALA increases the complete resection rate of malignant gliomas by about 1.4 times, and reduces the size of unresectable malignant gliomas to $\frac{1}{16}$, and therefore, it may be effectively used in preventing the recurrence of malignant gliomas.

However, since most contrast agents including 5-ALA which are used during optical diagnosis and surgery are non-specific to a lesion, accurate diagnosis and surgery are difficult. Therefore, to impart target specificity to contrast agents, a method of crosslinking contrast agents with a tumor-specific ligand such as a lesion-specific peptide, antibody, or polysaccharide via a covalent bond has been actively employed. However, when crosslinked via a covalent bond, new problems arise, such as reduction in chemical structure stability and targetability of the complex, and side effects in the human body, and thus accurate diagnosis and surgical resection of cancer are difficult.

Ma et al., Targeted Delivery of 5 Aminolevulinic Acid by Multifunctional Hollow Mesoporous Silica Nanoparticles for Photodynamic Skin Cancer Therapy ACS Appl. Mater. Interfaces 2015, 7, 10671-10676 discloses nanoparticles, in which silica nanoparticles having a hollow structure are prepared, and 5-ALA is loaded inside the hollow structure, and folic acid is conjugated onto the surface of the nanoparticles to provide a targeting moiety which specifically binds with folate receptor alpha overexpressed on some epithelial carcinoma cells. However, it is difficult to apply the nanoparticles to clinical practice, because the final product after preparation continuously releases 5-ALA, and hollow silica is not a natural material but an inorganic material.

Jin et al., Intracellular Dual Fluorescent Lightup Bioprobes for Image-Guided Photodynamic Cancer Therapy Small 2016, 12, No. 28, 3870-3878 discloses a complex prepared by conjugating a targeting moiety biotin with polyethylene glycol (PEG), methyl aminolevulinate (MAL), and tetraphenylene (TEP, Aggregation induced fluorescence emission) via a covalent bond. It is disclosed that the complex selectively delivers the two fluorescence-inducing substances (MAL, TEP) to cancer cells. However, there are concerns that the preparation process becomes overly complex due to chemical bonding through several stages, biotin's own targetability may be reduced due to the covalent binding of the fluorescence-inducing substance to the targeting moiety, and efficacy stability may be reduced due to the structural change of biotin.

DESCRIPTION OF EMBODIMENTS

Technical Problem

An aspect of the present disclosure provides a drug carrier for a contrast agent which may be used in cancer diagnosis, the drug carrier capable of targeting cancer cells without using a covalent bond with a tumor-specific ligand.

Another aspect of the present disclosure provides medical use of the drug carrier in cancer diagnosis.

Still another aspect of the present disclosure provides a method of preparing the drug carrier.

Solution to Problem

An aspect of the present disclosure provides a micelle structured nanocarrier including an aqueous phase ingredient, the aqueous phase ingredient obtained by dispersing, in water, a water-in-oil nanoemulsion including an oil phase ingredient, a surfactant, and the aqueous phase ingredient to remove the oil phase ingredient, wherein the aqueous phase ingredient includes a cancer cell fluorescence-inducing substance and a cancer cell-targeting polysaccharide.

Another aspect of the present disclosure provides a pharmaceutical composition for cancer diagnosis, the pharmaceutical composition including the micelle structured nanocarrier according to an aspect of the present disclosure.

Still another aspect of the present disclosure provides a method of preparing the micelle structured nanocarrier according to an aspect of the present disclosure.

Advantageous Effects of Disclosure

A nanocarrier according to an aspect of the present disclosure may include both of a cancer cell fluorescence-inducing substance and a cancer cell-targeting polysaccharide inside an aqueous phase of the nanocarrier to selectively deliver the fluorescence-inducing substance not to normal cells but to cancer cells. Accordingly, a cancerous tissue may be clearly distinguished from a normal tissue by fluorescence emitted when the cancerous tissue is irradiated with a specific excitation wavelength. Thus, this is expected to achieve a precise diagnosis and efficient surgical resection of a cancerous lesion site, and to ultimately maximize therapeutic effects on cancer. Further, since the nanocarrier has nanoparticle size homogeneity and excellent thermodynamic stability, and its long-term storage is also possible, the nanocarrier is a pharmaceutically superior agent. Furthermore, since the nanocarrier may be prepared in a relatively simple manner and its mass production is possible, the nanocarrier is economical.

BRIEF DESCRIPTION OF DRAWINGS

FIG. 2 illustrates that no fluorescence was generated before uptake of 5-ALA into a cancer cell whereas fluorescence was generated after uptake of 5-ALA into the cancer cell (A); and illustrates a mechanism of protoporphyrin IX production induced by 5-ALA inside the cancer cell and a mechanism of emission of fluorescence of 635 nm upon irradiation of protoporphyrin IX with light of a wavelength of 410 nm (B);

BEST MODE

Figure 1:
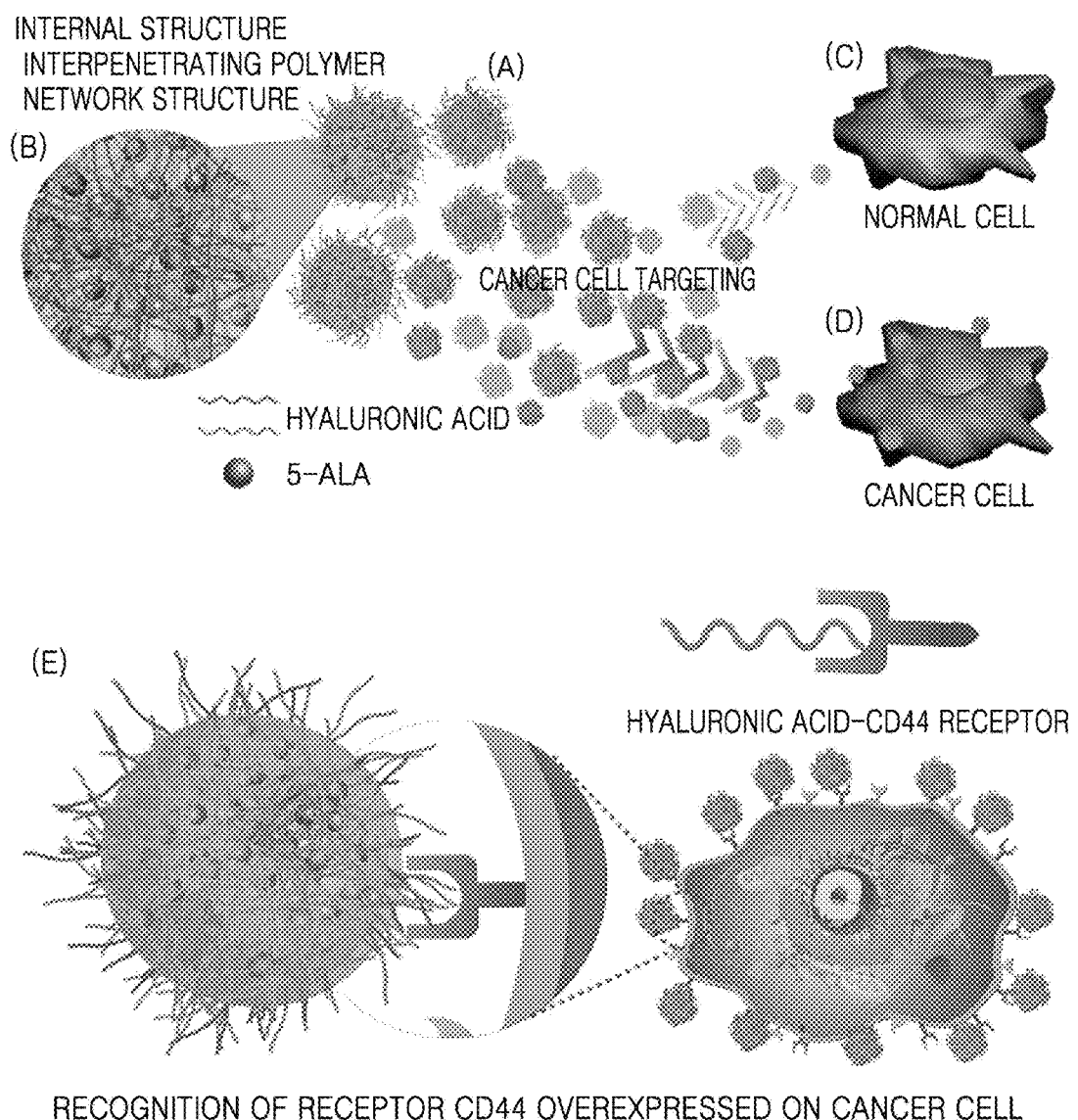
FIG. 1 illustrates, according to an embodiment of the present disclosure, a micelle structured nanocarrier inside which is contained 5-ALA and hyaluronic acid (A), an interpenetrating polymer network structure of the nanocarrier (B), no response of the nanocarrier to a normal cell when it encounters the normal cell and a cancer cell (C), and a cellular interaction between the hyaluronic acid protruding from the nanocarrier and a CD44 receptor on the surface of a cancer cell (D, E)

Hereinafter, the present disclosure will be described in more detail.

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. The numerical values described herein are considered to include the meaning of "about", unless otherwise specified. In the present disclosure, a component "including" a particular element means that it does not exclude another element, but it further includes another element, unless otherwise mentioned. The contents of all the publications disclosed as references herein are incorporated in the present disclosure.

The present inventors have studied a drug carrier capable of targeting cancer cells without using a covalent bond between a cancer cell fluorescence-inducing substance such as 5-ALA and a tumor-specific ligand, and as a result, they found that when a nanocarrier is prepared by including both of a cancer cell fluorescence-inducing substance and a cancer cell-targeting polysaccharide inside an aqueous phase of the nanocarrier, the cancer cell fluorescence-inducing substance is selectively internalized into cancer cells, thereby identifying a cancerous tissue by fluorescence. The nanocarrier may be obtained by mixing an oil phase ingredient; a surfactant; and the aqueous phase ingredient including the cancer cell fluorescence-inducing substance and the cancer cell-targeting polysaccharide to prepare a water-in-oil nanoemulsion, and then dispersing the nanoemulsion in water to remove an oil phase ingredient.

Accordingly, an aspect of the present disclosure provides a micelle structured nanocarrier including an aqueous phase ingredient, the aqueous phase ingredient obtained by dispersing, in water, a water-in-oil nanoemulsion including an oil phase ingredient, a surfactant, and the aqueous phase ingredient to remove the oil phase ingredient, wherein the aqueous phase ingredient includes a cancer cell fluorescence-inducing substance and a cancer cell-targeting polysaccharide.

Consequently, the nanocarrier is a micelle structured nanocarrier that includes the aqueous phase including the cancer cell fluorescence-inducing substance and the cancer cell-targeting polysaccharide inside thereof and the surfactant on the surface thereof.

As used herein, the term "oil phase ingredient" refers to an oil-soluble substance that is dissolved in oil. The oil phase ingredient may be any oil which may be used in the art for the preparation of the nanoemulsion, and for example, may be an oil selected from the group consisting of soybean oil, olive oil, grape seed oil, canola oil, corn oil, mineral oil, silicone oil, castor oil, paraffin oil, and any combination thereof. In a specific embodiment, the oil phase ingredient may be soybean oil.

As used herein, the term "aqueous phase ingredient" refers to a water-soluble substance that is dissolved in water. In a specific embodiment, the aqueous phase ingredient is an aqueous solution including the cancer cell fluorescence-inducing substance and the cancer cell-targeting polysaccharide in water as a medium.

As used herein, the term "cancer cell fluorescence-inducing substance" refers to any substance that is internalized into cancer cells in vivo to generate a fluorescent substance. The cancer cell fluorescence-inducing substance may be any substance that is known in the art to be internalized into cancer cells to generate a fluorescent substance or may be found in the future. For example, a substance capable of generating a fluorescent substance such as protoporphyrin IX may be a cancer cell fluorescence-inducing substance selected from the group consisting of heme, hemin, zinc protoporphyrin, magnesium protoporphyrin, hematoporphyrin, benzoporphyrin, metalloporphyrin, 5-aminolevulinic acid, texaphyrins, chlorins, purpurins, bacteriochlorins, phthalocyanine, naphthalocyanine, and derivatives thereof, and any combination thereof, but is not limited thereto. In a specific embodiment, the cancer cell fluorescence-inducing substance is 5-ALA.

As used herein, the term "cancer cell-targeting polysaccharide" refers to any polysaccharide capable of selectively binding to a molecule or a receptor overexpressed on the surface of cancer cells. The cancer cell-targeting polysaccharide may be any cancer cell-targeting polysaccharide that is known in the art to selectively bind to a molecule or a receptor overexpressed on the surface of cancer cells or may be found in the future.

The cancer cell-targeting polysaccharide may be hyaluronic acid or a cancer cell-targeting ligand-binding polysaccharide.

As used herein, the term "cancer cell-targeting ligand-binding polysaccharide" refers to a complex of a polysaccharide and any cancer cell-targeting ligand capable of selectively binding to a marker, i.e., a molecule or a receptor overexpressed on the surface of cancer cells via a covalent bond. The marker overexpressed on the surface of cancer cells, the cancer cell-targeting ligand capable of binding thereto, and a method of binding the cancer cell-targeting ligand to the polysaccharide are well known in the art. The cancer cell-targeting ligand may be an aptamer, an antibody, or a peptide, and the polysaccharide may be for example selected from the group consisting of alginic acid, chitosan, pectin, beta-glucan, cellulose, gelatin, hemicellulose, galactomannan, inulin, gum, and chitin, but is not limited thereto.

In a specific embodiment, the targeting ligand may be folic acid.

In a specific embodiment, the cancer cell-targeting polysaccharide may be hyaluronic acid. The hyaluronic acid may bind to CD44 which is a hyaluronic acid receptor specifically overexpressed on cancer cells, and thus hyaluronic acid serves as the cancer cell-targeting polysaccharide. Unlike hyaluronic acid, most natural polysaccharides such as alginic acid, chitosan, pectin, etc. are known to have no specific cancer cell-binding ability, but these polysaccharides may be provided with targetability by covalently binding to the cancer cell-targeting ligand. Therefore, the cancer cell-targeting ligand-binding polysaccharide may bind to a receptor specifically overexpressed on the surface of cancer cells, wherein the receptor is able to bind with the ligand, and thus it may serve as a cancer cell-targeting polysaccharide.

In a specific embodiment, the cancer cell-targeting polysaccharide may be a cancer cell-targeting ligand-binding alginic acid. The alginic acid is a block copolymer consisting of mannuronic acid (M) and gluronic acid (G), and generally extracted from seaweeds.

As used herein, the term "aptamer" refers to any biopolymeric substance having a single or double stranded DNA or RNA form, which may specifically interacts and bind with a target protein via a three-dimensional bond with the target protein. The aptamers are known to bind with metal ions, small molecules, proteins, and even whole cells according to the kind thereof. There is also an aptamer specifically binding to a protein which may be used as a biomarker.

In a specific embodiment, the aptamer may be an aptamer binding to mucin, particularly mucin 1 (Muc1). Mucin is an internal transmembrane domain which is a cell surface-associated glycoprotein attached to the cell. Among mucin, mucin 1 (Muc1) contains a hydrophobic membrane-spanning domain with 31 amino acids, a cytoplasmic domain with 69 amino acids, and an extracellular domain consisting of nearly identical repeats with 20 amino acids. Muc1 is over-expressed in almost all human epithelial cancer cells including breast cancer, stomach cancer, colorectal cancer, lung cancer, prostate cancer, ovarian cancer, pancreatic cancer, and bladder cancer. Moreover, the expression of MUC1 in these tissues lacks otherwise regular expression patterns, resulting in a ubiquitous, random expression of the protein all over the cell surface. Therefore, an aptamer (Anti-MUC1 Aptamer) specifically binding to mucin 1 (MUC1) may serve as the cancer cell-targeting ligand, and a polysaccharide binding thereto may be used as the cancer cell-targeting polysaccharide.

The antibody may be any antibody which is known to selectively bind to cancer cells, and specific examples thereof are widely known in the art, and a preparation method thereof may be performed by a person skilled in the art using knowledge known in the art.

The folic acid may specifically bind to folate receptor-alpha which is known to be overexpressed on ovarian cancer, etc. Overexpression of folate receptor-alpha is found in 90-95% of ovarian cancer. In a specific embodiment, the folic acid may bind to alginic acid to form a cancer cell-targeting polysaccharide. Specifically, a carboxyl group ($COOH^-$) of alginic acid and an amine group ($NH_2$) of folic acid are covalently bound to each other to form the cancer cell-targeting polysaccharide.

In a specific embodiment, prepared was a micelle structured nanocarrier including folic acid-binding alginic acid as the cancer cell-targeting polysaccharide and 5-ALA as the cancer cell fluorescence-inducing substance, and ovarian cancer cells (SK-OV-3) where folate receptor-alpha was overexpressed were treated with the nanocarrier. As a result, the nanocarrier was selectively internalized into the cancer cells, and selective fluorescence-inducing effect by protoporphyrin IX was observed.

In a specific embodiment, the micelle structured nanocarrier may have nanoparticles of an interpenetrating polymer network structure (IPN).

As used herein, the interpenetrating polymer network structure refers to an entangled network formed by two or more components without a covalent bond. An illustration of an interpenetrating polymer network structure of a nanocarrier according to an embodiment of the present disclosure is shown in FIG. 1(B). Since the micelle structured nanocarrier may have the interpenetrating polymer network structure, the cancer cell fluorescence-inducing substance and the cancer cell-targeting polysaccharide included in the aqueous phase ingredient thereof may be physically encapsulated, thereby increasing mechanical strength and thermodynamic stability. Further, the nanocarrier may have a high absolute value of a zeta potential on the surface due to cations or anions of the cancer cell-targeting polysaccharide. Due to a repulsive force between particles by such a high zeta potential, Ostwald ripening may be prevented to increase stability of the nanocarrier. As a result of experiments, the size change of the prepared nanocarrier was measured over time using a dynamic scattering light instrument while nanoparticles according to an embodiment of the present disclosure were refrigerated for 60 days, and it was found that the diameter of the nanocarrier hardly changed, indicating that the nanocarrier is thermodynamically very stable (see Experimental Example 3 and FIG. 4).

The micelle structured nanocarrier may have an average particle size of about 200 nm or less. In a specific embodiment, the micelle structured nanocarrier may be 50 nm to 150 nm.

In a specific embodiment, the zeta potential of the micelle structured nanocarrier may be −10 mV to −50 mV or 10 mV to 50 mV, and more specifically −10 mV to −30 mV or 10 mV to 30 mV. The zeta potential is a value obtained when the cancer cell-targeting polysaccharide is negatively charged in the aqueous phase. The surface zeta potential value is changed by an ionic bond by an interaction between the substances encapsulated inside the nanocarrier. When nanoparticles have a low zeta potential within the above range, a repulsive force between particles is increased to prevent a phenomenon such as Ostwald ripening, thereby maintaining stable nanoparticles.

In a specific embodiment, the nanoparticle may have an average particle size of 200 nm or less, and a zeta potential value of −10 mV to −30 mV. In terms of homogeneity of the nanoparticles, the nanoparticle may have an average particle size of about 100 nm, and a zeta potential value of −10 mV to −30 mV.

Figure 3:
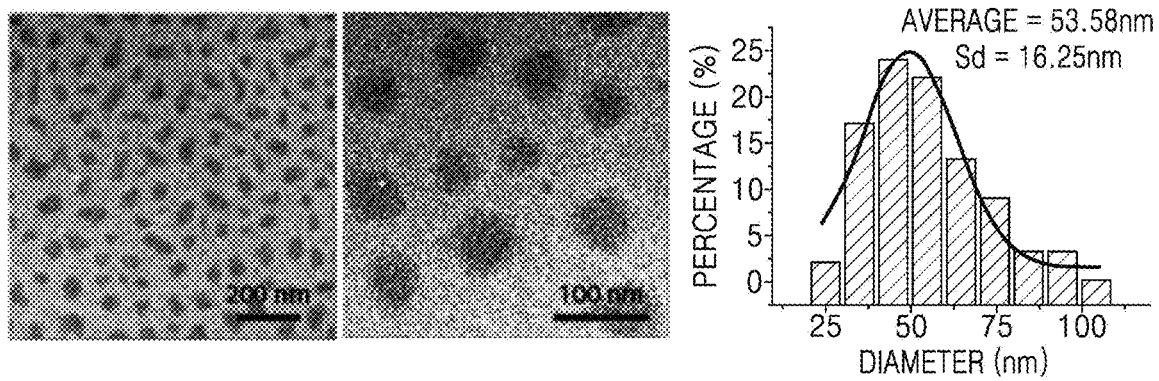
FIG. 3 shows nanocarrier images and nanocarrier sizes obtained by observing and measuring a nanocarrier prepared in Example 1 using a transmission electron microscope at low and high magnifications.

The particle size and zeta potential of the micelle structured nanocarrier (Examples 1 to 3) prepared according to an embodiment of the present disclosure were measured, and the results are shown in Table 1 and FIG. 3. The result of FIG. 3 showed that the average particle size and zeta potential were changed as a content ratio of the aqueous phase ingredient is changed. It was found that as the content ratio of the amphoteric molecule 5-ALA increases, the zeta potential was decreased, and the size of the nanoparticle was also decreased. It seems that as the ionic bond between the anionic polysaccharide and the amphoteric 5-ALA inside the nanocarrier increases, the surface zeta potential of the nanocarrier decreases.

In a specific embodiment, the nanoemulsion for the preparation of the micelle structured nanocarrier may include 70% by weight to 80% by weight of the oil phase ingredient, 10% by weight to 20% by weight of the aqueous phase ingredient, and 5% by weight to 15% by weight of the surfactant, based on the total weight of the nanoemulsion. The surfactant may include at least one of a single surfactant and a cosurfactant.

The nanoemulsion may control the size of the aqueous phase nanoparticle of the water-in-oil nanoemulsion within the above range of the ingredient, and may maintain stability of the aqueous phase nanoparticle. Particularly, when the weight ratio of the aqueous phase ingredient is larger than the weight ratio of the surfactant, based on the total weight of the nanoemulsion, nano-sized particles may be formed, and stability of the particles are also excellent.

As used herein, the term "cosurfactant" refers to a mixture of two or more surfactants, and may be used in the preparation of the nanoemulsion having nano-sized particles. The cosurfactant may have a desired HLB value by combination of surfactants having different HLB values. HLB is a measure of hydrophilicity and hydrophobicity. A surfactant has its own HLB value of 0 to 20. The value closer to 0 means more hydrophobic, and the value closer to 20 means more hydrophilic. A method of determining HLB of a cosurfactant based on hydrophilic-hydrophobic balance (HLB) values of surfactants is known in the art.

In a specific embodiment, the surfactant may be a cosurfactant having the HLB value of 6 to 9. The cosurfactant having the HLB value of 6 to 9 may be more favorable in terms of maintaining the particle size of the nanoemulsion in the nano size.

In a specific embodiment, the cosurfactant may be a mixture containing sorbitan fatty acid ester (Span) and polyoxyethylene sorbitan fatty acid ester (Tween) and having the HLB value of 6 to 9.

In a specific embodiment, the surfactant may be a cosurfactant containing Tween 80 (HLB 15) and Span 80 (HLB 4.3) and having the HLB value of about 7.

Another aspect of the present disclosure provides a pharmaceutical composition for cancer diagnosis, the pharmaceutical composition including the nanocarrier according to an aspect of the present disclosure.

The above description of the micelle structured nanocarrier according to an aspect of the present disclosure may be also applied to a detailed description of the nanocarrier included in the pharmaceutical composition for cancer diagnosis.

The micelle structured nanocarrier according to an aspect of the present disclosure may selectively deliver the cancer cell fluorescence-inducing substance not to normal cells but to cancer cells, and therefore, it may be used as a contrast agent that clearly distinguishes cancer cells from the normal tissue by the fluorescent substance induced by the fluorescence-inducing substance internalized into cancer cells.

FIG. 1 illustrates a micelle structured nanocarrier containing 5-ALA and hyaluronic acid inside thereof according to an embodiment of the present disclosure (A), an interpenetrating polymer network structure of the nanocarrier (B), no response of the nanocarrier to a normal cell when it encounters the normal cell and a cancer cell (C), and a cellular interaction between the hyaluronic acid protruding from the nanocarrier and CD44 receptor on the surface of cancer cell (D Hyaluronic acid is encapsulated in the nanocarrier, but a portion of hyaluronic acid protrudes from the surface of the nanocarrier due to its chain-shaped molecular structure.

As shown in FIG. 1 (D, E), the micelle structured nanocarrier may selectively bind to cancer cells by binding to CD44 receptor overexpressed on the surface of cancer cell through the hyaluronic acid encapsulated in the nanocarrier. Specifically, the binding between the hyaluronic acid and CD44 receptor is attributed to a specific interaction between the chain structure present in hyaluronic acid and CD44 receptor overexpressed on the cancer cell. 5-ALA in the nanocarrier binding to the surface of cancer cell may be internalized via CD44 receptor-mediated endocytosis. In the case of cancer cells, porphobilinogen deaminase which is a rate-limiting enzyme needed in protoporphyrin IX (PpIX) biosynthesis is increased, and ferrochelatase which is an enzyme converting PpIX into heme is decreased, as compared to normal cells. Therefore, when a high concentration of 5-ALA is internalized from outside, PpIX production in cancer cells is remarkably promoted, as compared to normal cells.

The micelle structured nanocarrier does not generate fluorescence before internalization of 5-ALA into cancer cells. However, when 5-ALA is internalized into cancer cells by the targeting effect of hyaluronic acid, 5-ALA is induced to protoporphyrin IX by mitochondria inside the cytoplasm of cancer cells, and the produced protoporphyrin IX emits fluorescence of 635 nm when irradiated with light of a wavelength of 410 nm. Selective uptake of the micelle structured nanocarrier according to an embodiment by cancer cells, and emitting of fluorescence thereby are shown in FIG. 2. The micelle structured nanocarrier according to an embodiment of the present disclosure may clearly distinguish cancer cells from a normal tissue by fluorescence, thereby being effectively used in cancer diagnosis.

As a result of a practical experiment, it was confirmed that the nanocarrier according to an embodiment of the present disclosure does not generate fluorescence with respect to normal cells, whereas selectively generates fluorescence with respect to cancer cells. The micelle structured nanocarrier including the aqueous phase including hyaluronic acid and 5-ALA prepared according to Example 1 and a nanocarrier (Comparative Example 1) including, instead of hyaluronic acid, alginic acid which is not a cancer cell-targeting polysaccharide were treated to 4 different kinds of cells (fibroblast, glioma, lung carcinoma, and gastric adenocarcinoma). As a result, the alginic acid-based nanocarrier did not generate selective fluorescence with respect to cancer cells, whereas the hyaluronic acid-based nanocarrier generated selective fluorescence with respect to cancer cells (FIGS. 10 to 13).

The "composition for cancer diagnosis" includes all of those used as a contrast agent to diagnose the presence of cancer as well as to monitor the treatment response or the severity of cancer during cancer therapy. Further, it is a concept including use of the contrast agent to clearly distinguish a cancerous tissue from a normal tissue during surgical resection of the cancerous tissue. In addition, it is construed to include any beneficial application that may be obtained by distinguishing a cancerous tissue from a normal tissue by fluorescence.

The cancer may be any cancer which may be targeted by the cancer cell-targeting polysaccharide and where the fluorescent substance may be induced from the cancer cell fluorescence-inducing substance, and may differ depending on the specific kind of the cancer cell fluorescence-inducing substance and/or the cancer cell-targeting polysaccharide. For example, the cancer may include brain tumor, lung cancer, stomach cancer, and ovarian cancer, but is not limited thereto.

In a specific embodiment, the micelle structured nanocarrier is a nanocarrier showing no significant toxicity when administered into a living body.

In a specific embodiment, the nanocarrier may include, as its raw materials, the cancer cell-targeting polysaccharide including a biocompatible polymer such as hyaluronic acid, alginic acid, or chitosan, etc. which has excellent biocompatibility, and 5-aminolevulinic acid as the cancer cell fluorescence-inducing substance which is also a non-toxic substance already present in a living body, and therefore, the nanocarrier may be used safely.

The nanocarrier according to an embodiment of the present disclosure was used to perform a cytotoxicity test for fibroblast and three kinds of cancer cells (glioma, lung carcinoma, and gastric adenocarcinoma) by CCK-8 assay, and the results are shown in FIGS. 6 to 9. According to FIGS. 6 to 9, a cell viability test of the four cell groups showed that the nanocarrier had no toxicity even at a concentration of 2 mg/mL.

An administration dose of the composition for cancer diagnosis may vary depending on the kind of the cancer cell fluorescence-inducing substance, and in a specific embodiment, when the cancer cell fluorescence-inducing substance is 5-ALA, the component may be administered in an amount of about 0.1 mg to about 1,000 mg for an adult male, and the dose may be appropriately increased or decreased by a physician according to race, sex, age, body weight, kind of carcinoma, and the like.

The pharmaceutical composition for cancer diagnosis may be prepared in any formulation capable of delivering the nanocarrier to a cancerous tissue for cancer diagnosis, and for example, may be prepared in an injectable formulation. When prepared in the injectable formulation, a non-toxic buffer solution isotonic to blood may be included as a diluent, and for example, a phosphate buffer solution of pH 7.4 may be used. The pharmaceutical composition may include other diluents or additives in addition to the buffer solution. The excipients and additives which may be added to the injectable formulation are widely known to those skilled in the art.

Still another aspect of the present disclosure provides a method of preparing the micelle structured nanocarrier according to an aspect of the present disclosure, the method including preparing the oil phase ingredient; preparing the surfactant; preparing the aqueous phase ingredient; mixing the oil phase ingredient, the surfactant, and the aqueous phase ingredient with stirring to prepare the water-in-oil nanoemulsion; and re-dispersing the water-in-oil nanoemulsion in water to remove an oil phase, thereby separating nanoparticles.

The above description of the micelle structured nanocarrier according to an aspect of the present disclosure may be also applied to a detailed description of the preparation method.

In a specific embodiment, the preparing of the aqueous phase ingredient may include preparing a first aqueous phase ingredient including the cancer cell-targeting polysaccharide; and preparing a second aqueous phase ingredient including the cancer cell fluorescence-inducing substance.

In the mixing of the oil phase ingredient, the surfactant, and the aqueous phase ingredient with stirring to prepare the water-in-oil nanoemulsion, the mixing with stirring may be performed by sonication, and according to a specific embodiment, high energy sonication may be performed for 5 minutes to 10 minutes using a 6 mm probe tip sonicator (Sonics, VC-750 amplitude 20-40%).

The re-dispersing of the water-in-oil nanoemulsion in water to remove an oil phase may be performed by simply removing the oil phase ingredient floating on the top of water during re-dispersing in water.

The preparation method may further include filtering, through a cellulose acetate syringe filter, the micelle structured nanocarrier which is obtained by removing the oil phase ingredient. Through the filtering, the nanocarrier may be obtained in a dispersed form without aggregation.

Mode of Disclosure

EXAMPLE

Hereinafter, the present disclosure will be described in detail with reference to the following Examples. However, these Examples are for illustrative purposes only, and the scope of the present disclosure is not intended to be limited thereby.

Example 1: Preparation of Hyaluronic Acid-Based Nanocarrier (1)

Sodium hyaluronate (Research grade from Lifecore, MW=91-175 kDa), purified soybean oil (Sigma), and 5-aminolevulinic acid (5-ALA: Sigma) were prepared. Span 80 (HLB value 4.3: Sigma) and Tween 80 (HLB value 15: Sigma) which are surfactants suitable for cell culture were prepared.

Based on hydrophilic-lipophilic balance (HLB) values, Span 80 and Tween 80 were used in combination to prepare a cosurfactant having an HLB value of 7. A first aqueous phase ingredient (1 w/w % sodium alginate aqueous solution) and a second aqueous phase ingredient (5 w/w % 5-ALA aqueous solution) were prepared.

A mixed solution prepared by mixing the prepared oil phase ingredient (soybean oil):cosurfactant:first aqueous phase ingredient:second aqueous phase ingredient at a weight ratio of 7:1:1:1 was stirred by sonication (Sonic, VC-750 model, amplitude: 40%) for 10 minutes. The sonication was performed until the opaque mixture became transparent or translucent to prepare a water-in-oil (w/o) nanoemulsion.

The nanoemulsion was re-dispersed in deionized water (DI water) to remove the oil phase ingredient, thereby separating nanoparticles. The separated nanoparticles were filtered through a cellulose acetate syringe filter (model DISMIC-13 from Advantec)) to prepare a nanocarrier solution dispersed in the aqueous phase.

Example 2: Preparation of Hyaluronic Acid-Based Nanocarrier (2)

A nanocarrier solution was prepared in the same manner as in Example 1, except that a 3% (w/w) 5-ALA aqueous solution was used instead of the 5% (w/w) 5-ALA aqueous solution as the second aqueous phase ingredient.

Example 3: Preparation of Hyaluronic Acid-Based Nanocarrier (3)

A nanocarrier solution was prepared in the same manner as in Example 1, except that a 1% (w/w) 5-ALA aqueous solution was used instead of the 5% (w/w) 5-ALA aqueous solution as the second aqueous phase ingredient.

Example 4: Preparation of Folic Acid-Alginic Acid (FA-Alg)-Based Nanocarrier

A nanocarrier solution was prepared in the same manner as in Example 1, except that a 1% (w/w) aqueous solution of folic acid covalently bound to sodium alginate (folic acid-alginic acid) was used instead of the 1% (w/w) sodium alginate aqueous solution.

A ratio of oil phase:cosurfactant:first aqueous phase:second aqueous phase used in the preparation of the nanoemulsions of Examples 1 to 4 are shown in Table 1 below.

TABLE 1

| | Weight ratio | | |
|---|---|---|---|
| | Oil phase | Cosurfactant Span80/Tween80 | Aqueous phase |
| Example 1 (5-ALA NC1) | 3.5 | 0.37/0.13 | 0.5 (1 wt % HA)/ 0.5 (1 wt % 5-ALA) |
| Example 2 (5-ALA NC2) | 3.5 | 0.37/0.13 | 0.5 (1 wt % HA)/ 0.5 (3 wt % 5-ALA) |
| Example 3 (5-ALA NC3) | 3.5 | 0.37/0.13 | 0.5 (1 wt % HA)/ 0.5 (5 wt % 5-ALA) |
| Example 4 (5-ALA NC4) | 3.5 | 0.37/0.13 | 0.5 (1 wt % FA-Alg)/ 0.5 (5 wt % 5-ALA) |

Comparative Example 1: Preparation of Alginic Acid-Based Nanoemulsion

A nanocarrier solution was prepared in the same manner as in Example 1, except that a 1% (w/w) sodium alginate aqueous solution was used instead of the 1% (w/w) sodium hyaluronate aqueous solution.

Experimental Example 1: Measurement of Nanocarrier Size

5 μl of the nanocarrier solution obtained in Example 1 was dropped on a 400-mesh copper grid of transmission electron microscope, followed by carefully wiping off around the grid with a towel. To remove excess water remaining in the grid, the grid was dried in a vacuum chamber for about 1 hour. After complete drying, the size of the nanocarrier was measured using a high magnification transmission electron microscope, and TEM images were photographed. The results are shown in FIG. 3. In the left of FIG. 3, TEM images of the nanocarrier which were observed at low and high magnifications are shown, and in the right of FIG. 3, a graph of the particle size based on the image analysis is shown. It was found that an average particle size of the nanocarrier was about 53.58 nm, and a standard deviation was 16.25 nm.

Experimental Example 2: Measurement of Size and Surface Charge of Nanocarrier

The average size and surface charge of the nanocarriers obtained in Examples 1 to 4 were measured using a dynamic light scattering (DLS) instrument (Zeta Nano ZS 3600, Malvern, UK). Each sample was measured in triplicate, and a mean value of the measured values was obtained. The results are shown in Table 2 below.

TABLE 2

| | Size (nm, DLS Z-avg) | Surface charge (mV) |
|---|---|---|
| Example 1 (5-ALA NC1) | 88.72 ± 1.5 | −10.8 ± 0.2 |
| Example 2 (5-ALA NC2) | 100.0 ± 1.8 | −12.9 ± 0.1 |
| Example 3 (5-ALA NC3) | 144.1 ± 2.6 | −22.5 ± 0.4 |
| Example 4 (5-ALA NC4) | 137.6 ± 2.7 | −10.7 ± 0.3 |

Experimental Example 3: Stability Test of Nanocarrier

The nanocarriers obtained in Examples 1 to 3 were refrigerated for 1 day to 60 days, and then an average particle size thereof was measured using a dynamic scattering light instrument. Each sample was measured in triplicate, and a mean value of the measured values was obtained. The results of measuring the average particle size of the nanocarriers over time are shown in FIG. 4.

Figure 4:
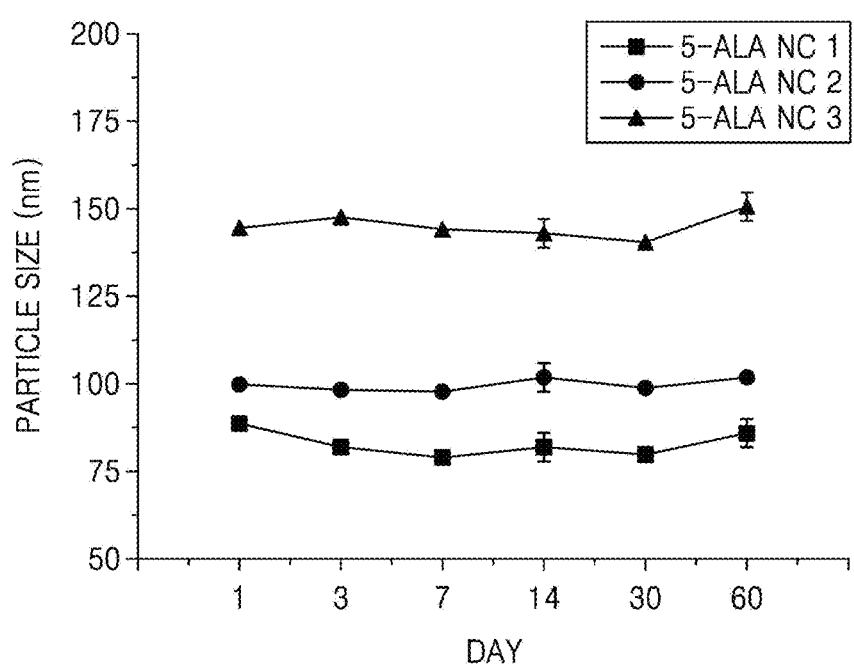
FIG. 4 shows a graph of average particle size measured using a dynamic scattering light (DLS) instrument after refrigerating nanocarriers of Examples 1 to 3 for 1 day to 60 days.

According to the result of FIG. 4, it was found that the average particle size was stably maintained in a nano size for 60 days or longer.

Experimental Example 4: Cancer Cell-Targeting Test of Nanocarrier

Cancer cells were treated with the nanocarrier obtained in Example 1, and it was examined whether protoporphyrin IX was actually induced in the cancer cells.

First, C6 (rat glioma), A549 (human lung carcinoma), and MKN-74 (human gastric adenocarcinoma) cell lines were obtained from the Korea Cell Line Bank (KCLB), and then each was cultured in RPMI 1640 medium (WELLGENE) supplemented with 1% penicillin-streptomycin (WELLGENE) and 10% fetal bovine serum (FBS; WELLGENE) in an incubator at 37° C., 5% $CO_2$, and subculturing was performed every two days.

Thereafter, the three kinds of cancer cell groups were cultured in a 24-well plate at a density of 1 mL ($5 \times 10^5$ cells/mL) for 24 hours, respectively. Then, the medium was replaced by a serum-free medium, and each of the cancer cells was treated with 100 μL (1 mg/mL concentration) of the nanocarrier obtained in Example 1, followed by incubation for 6 hours. To extract protoporphyrin IX in the cells, the cell culture medium was completely aspirated, and 100 μL of RIPA buffer solution was dropped to degrade cell membrane proteins. Absorbance of the extracted protoporphyrin IX was measured (FIG. 5B), and fluorescence spectra (FIG. 5C) was measured using a spectrofluorometer. Fluorescence spectrum (FIG. 5A) of the nanocarrier itself before treatment to the cancer cells was also measured using a spectrofluorometer.

Figure 5:
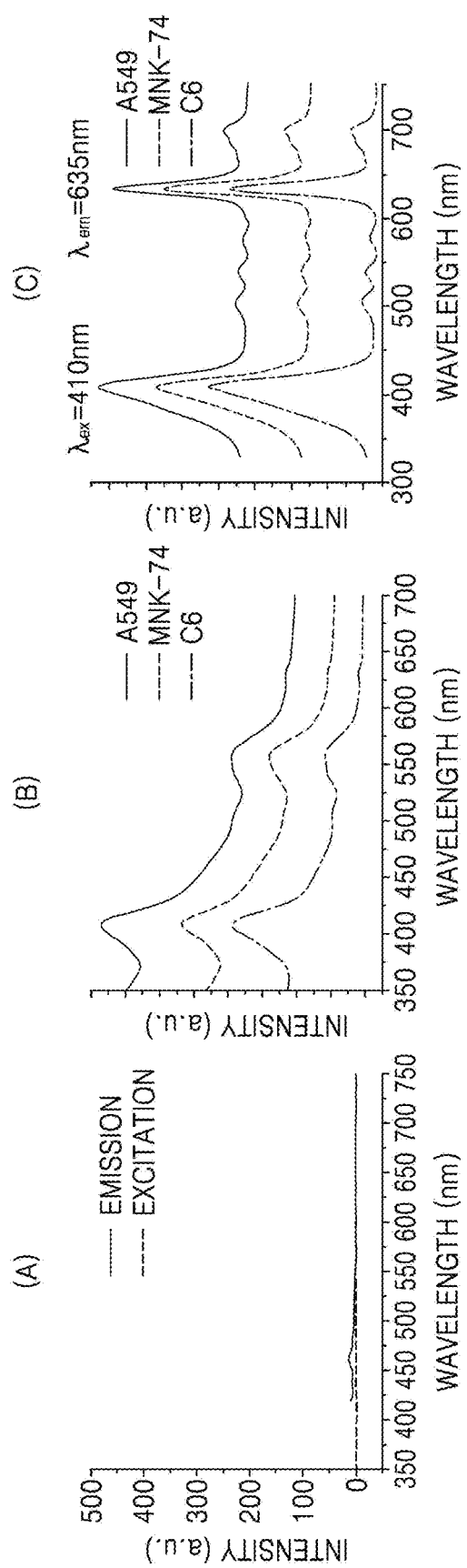
FIG. 5 shows a graph of absorbance of protoporphyrin IX after treating various cancer cells with the nanocarrier of Example 1 (B), fluorescence spectra measured using a spectrofluorometer (C), and a fluorescence spectrum of the nanocarrier itself before treatment of cancer cells (A)
Figure 6:
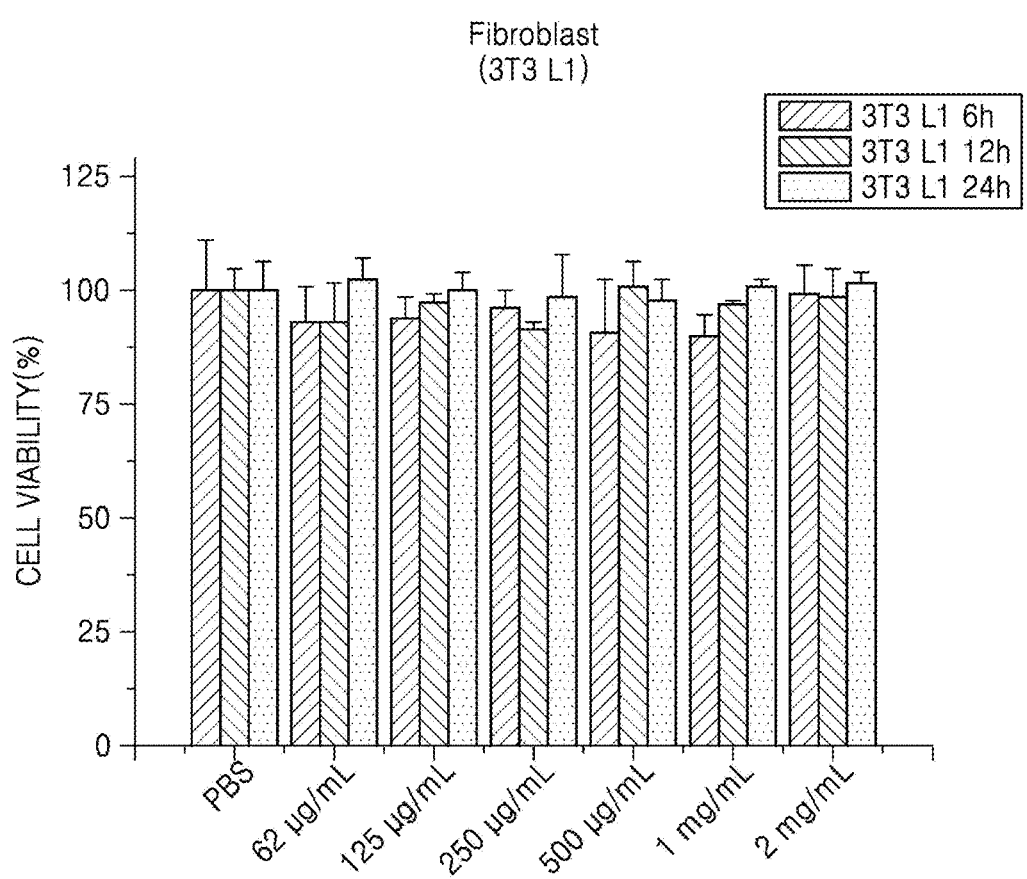
FIGS. 6 to 9 are graphs showing cell viability which was assessed by CCK-8 assay to examine cytotoxicity against fibroblasts and three kinds of cancer cells (glioma, lung carcinoma, and gastric adenocarcinoma)
Figure 7:
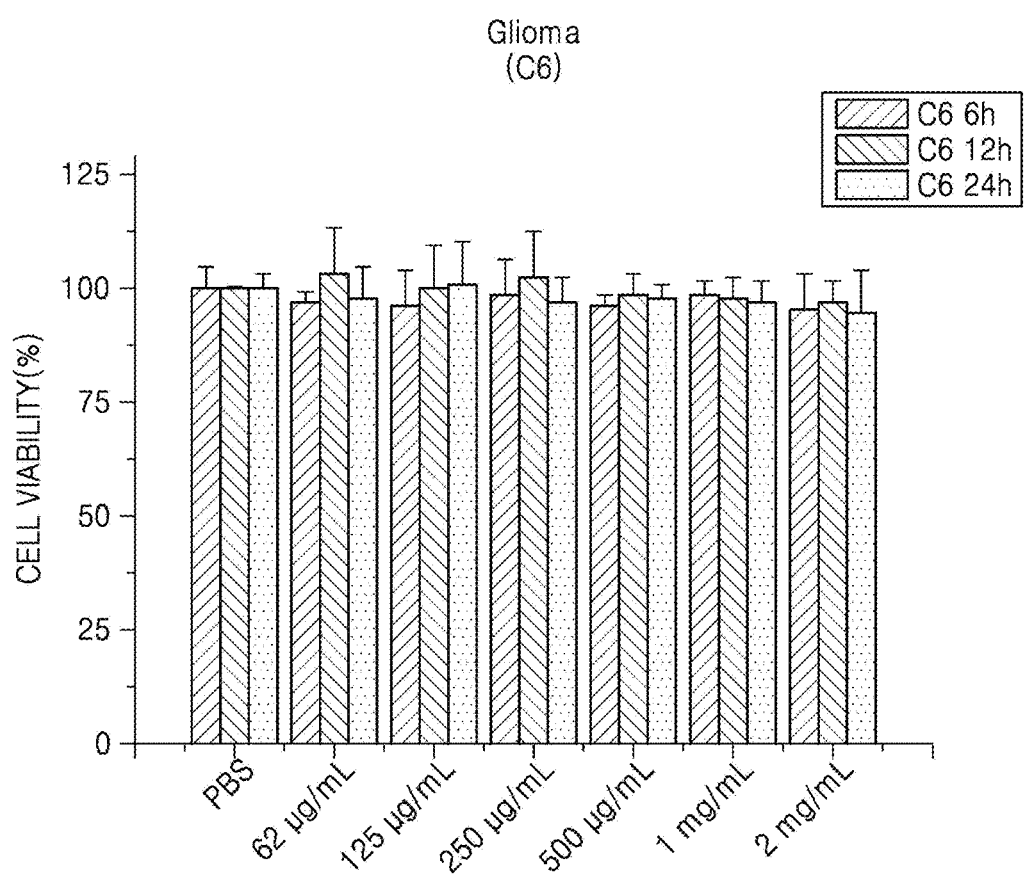
Figure 8:
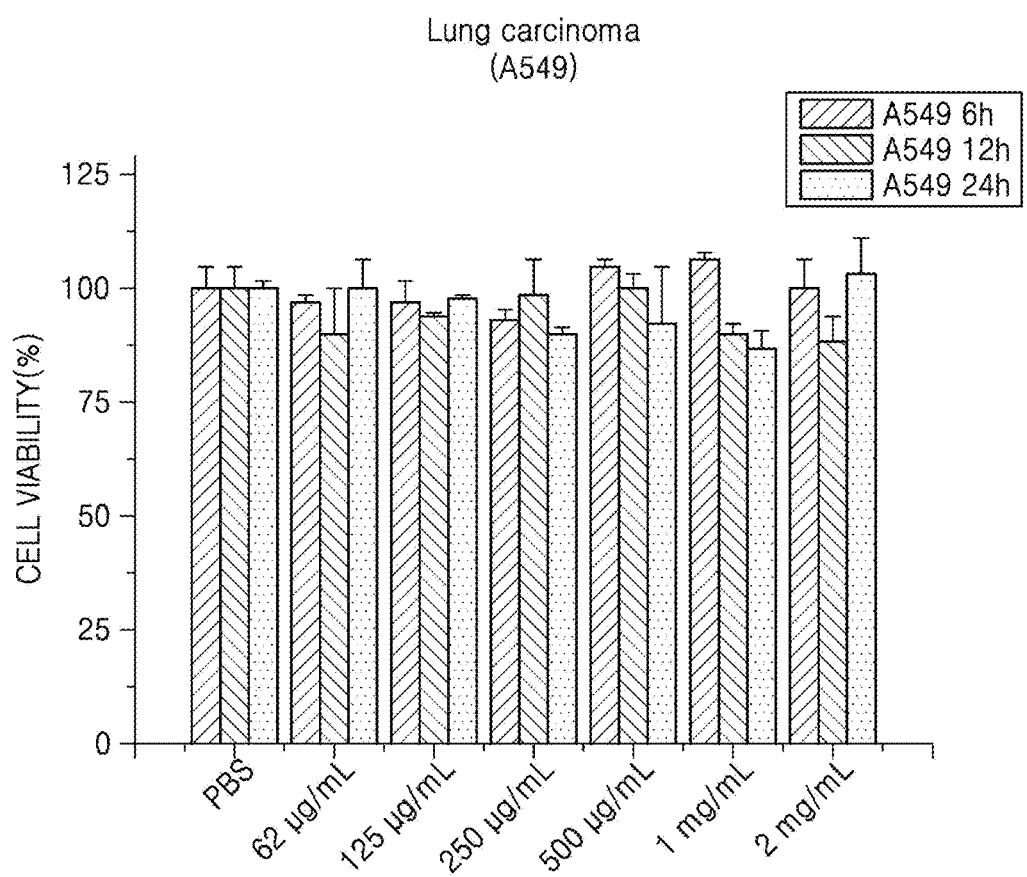
Figure 9:
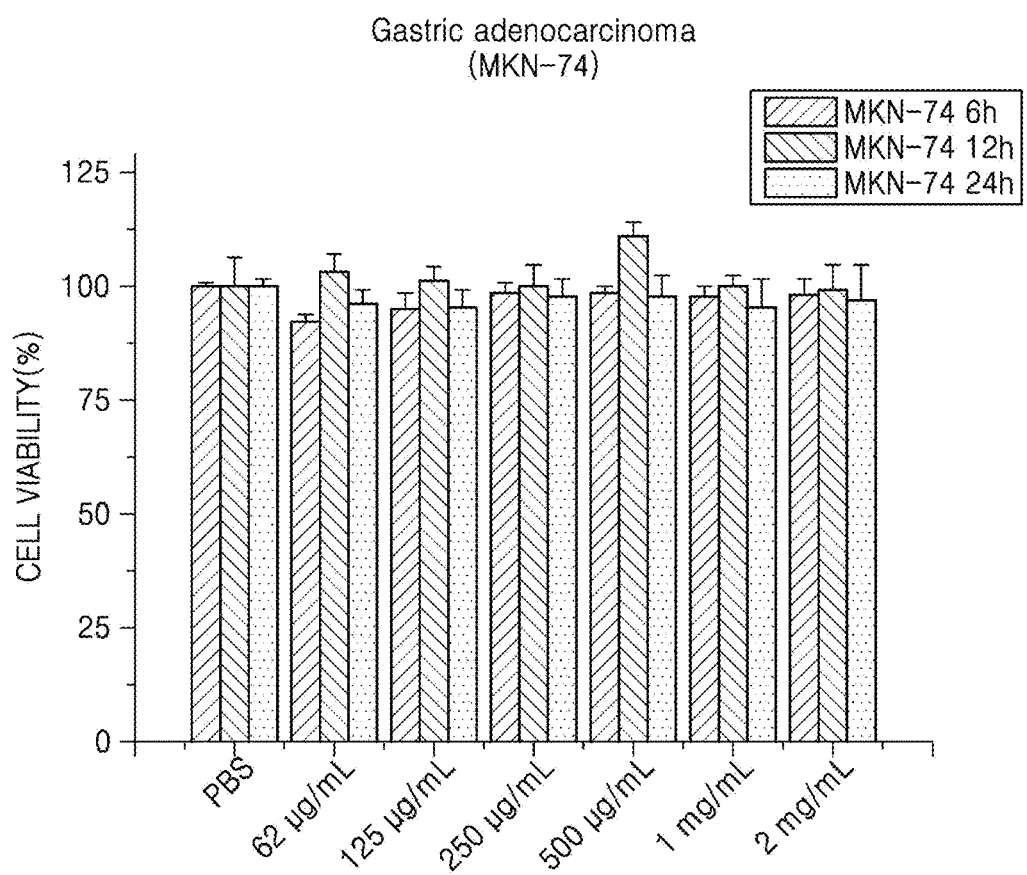
Figure 10:
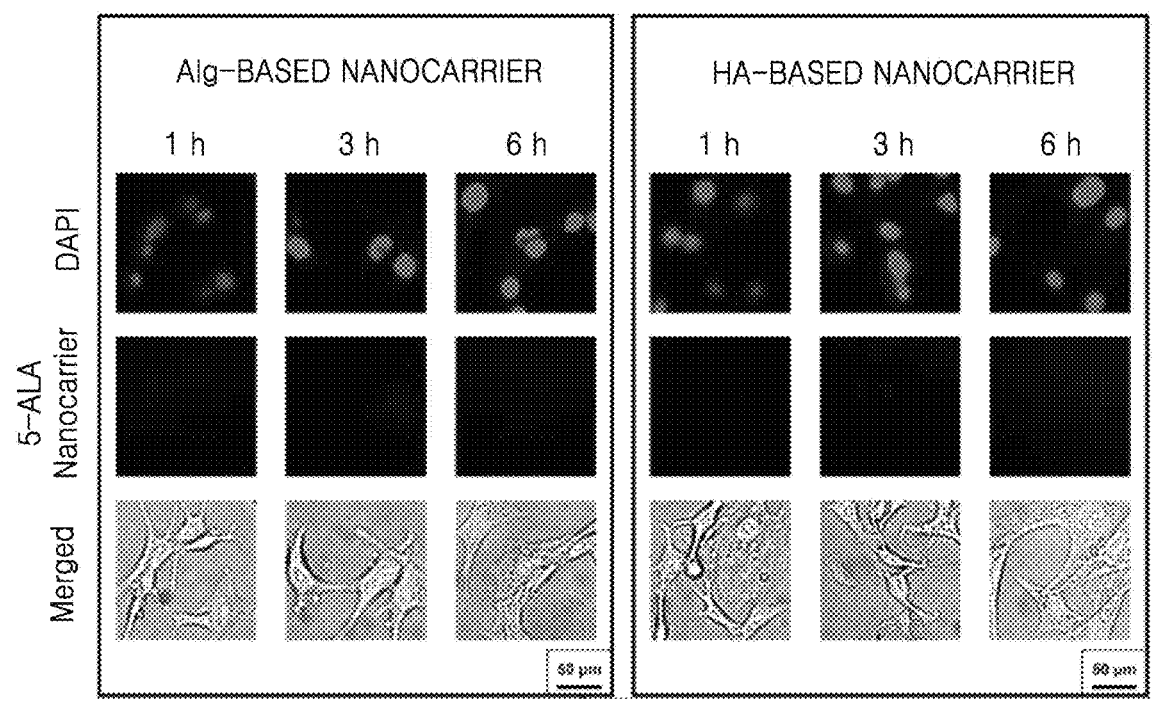
FIG. 10 shows fluorescence microscope images of DAPI and PpIX fluorescence which was observed after normal 3T3-L1 cells (mouse fibroblast) were treated with each of a hyaluronic acid-based nanocarrier (HA-based carrier) of Example 1 and an alginic acid-based nanocarrier (Alg-based carrier) of Comparative Example 1 and left for a predetermined time.
Figure 11:
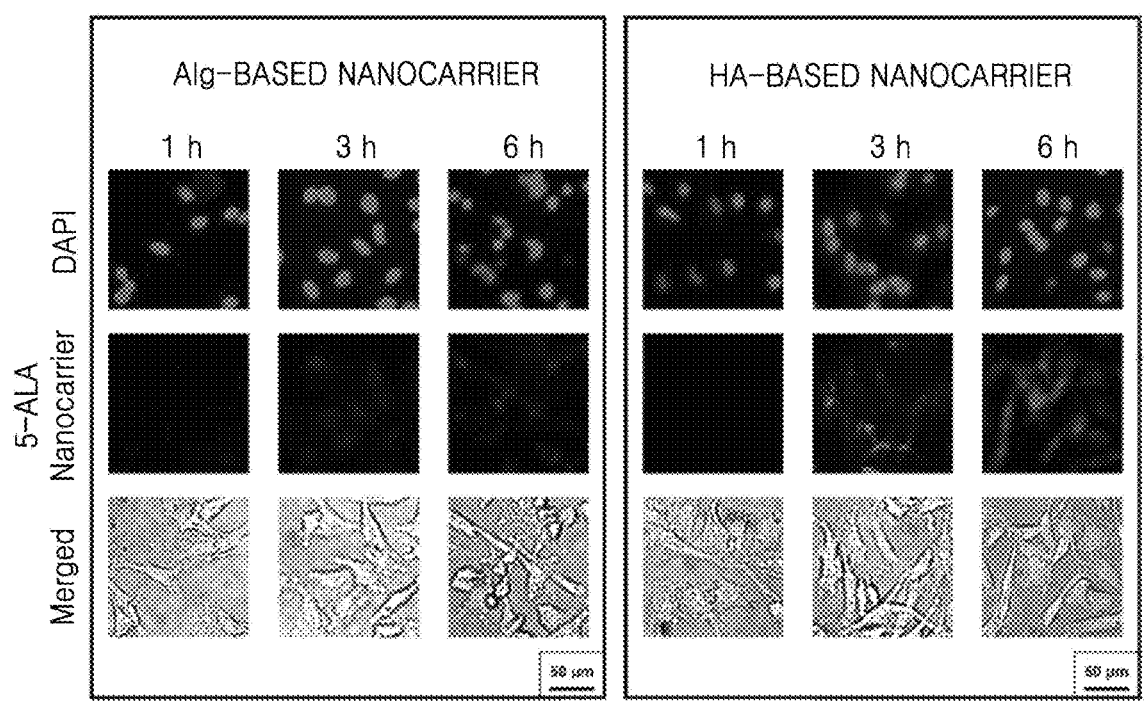
FIG. 11 shows fluorescence microscope images of DAPI and PpIX fluorescence which was observed after glioma cells were treated with each of the hyaluronic acid-based nanocarrier (HA-based carrier) of Example 1 and the alginic acid-based nanocarrier (Alg-based carrier) of Comparative Example 1 and left for a predetermined time.
Figure 12:
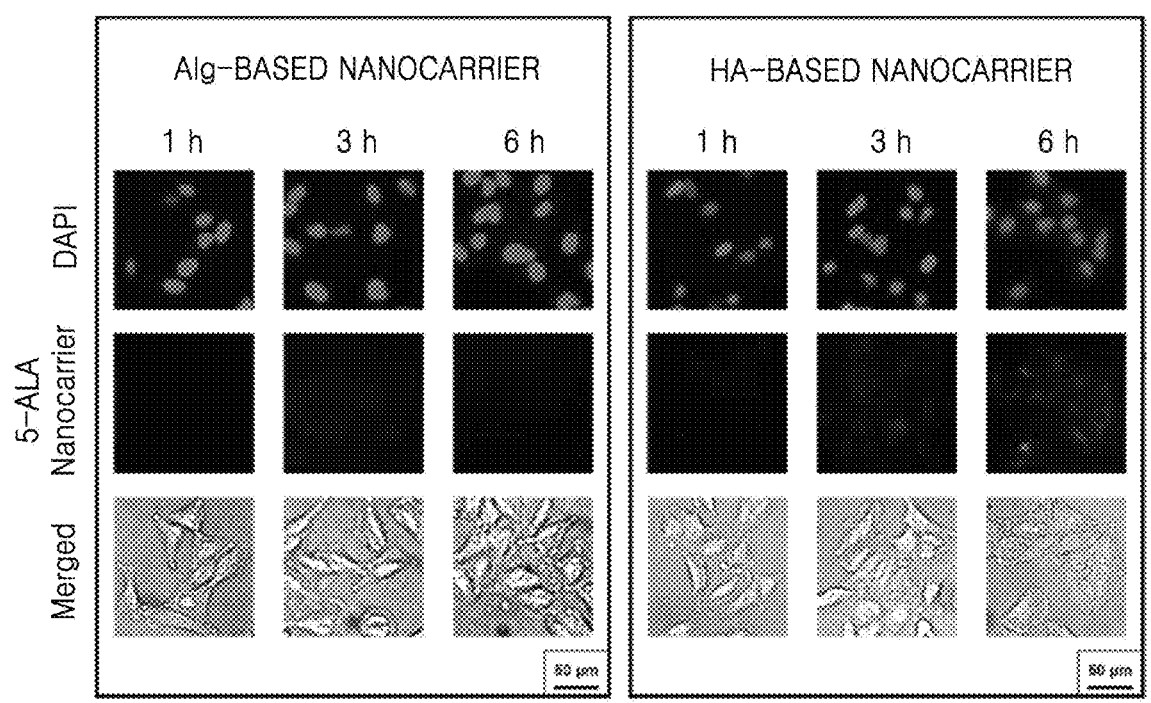
FIG. 12 shows fluorescence microscope images of DAPI and PpIX fluorescence which was observed after lung carcinoma cells were treated with each of the hyaluronic acid-based nanocarrier (HA-based carrier) of Example 1 and the alginic acid-based nanocarrier (Alg-based carrier) of Comparative Example 1 and left for a predetermined time.
Figure 13:
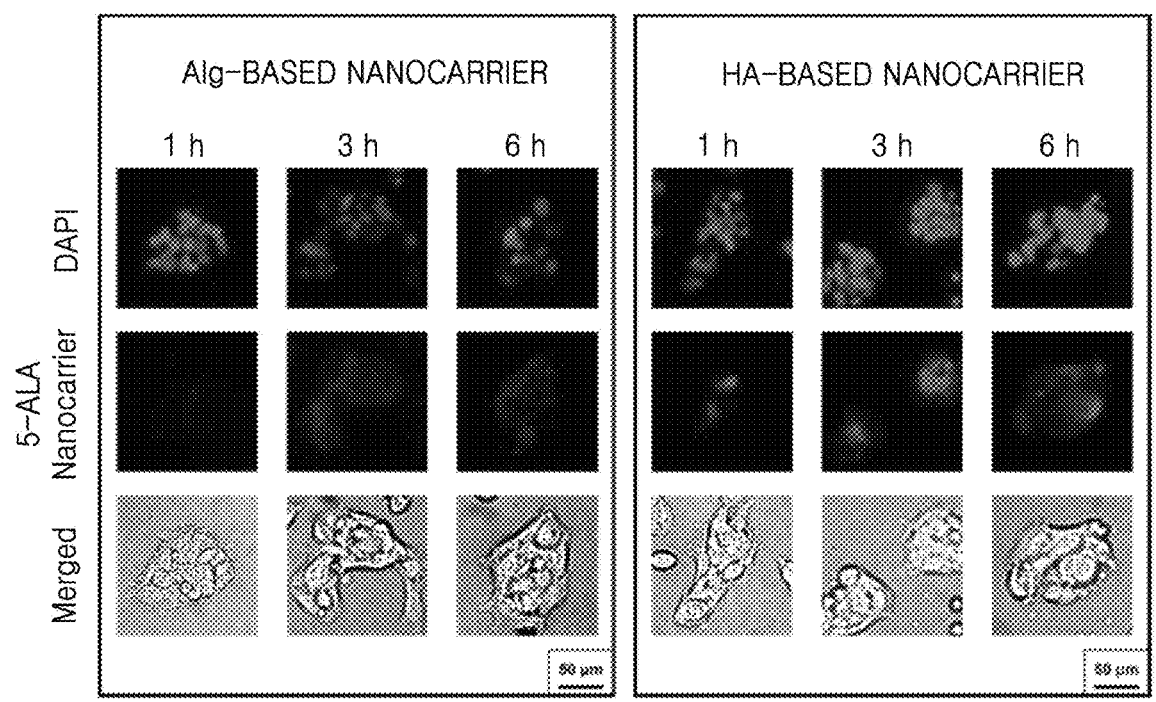
FIG. 13 shows fluorescence microscope images of DAPI and PpIX fluorescence which was observed after gastric adenocarcinoma cells were treated with each of the hyaluronic acid-based nanocarrier (HA-based carrier) of Example 1 and the alginic acid-based nanocarrier (Alg-based carrier) of Comparative Example 1 and left for a predetermined time.

The results are shown in FIG. 5.

According to the results of FIG. 5, the result of fluorescence spectrum of the nanocarrier itself (FIG. 5A) showed no excitation wavelength and no emission wavelength between a wavelength of 350 nm and a wavelength of 750 nm, whereas the nanocarrier-treated cancer cells showed absorbance peak of protoporphyrin IX (FIG. 5B), suggesting that protoporphyrin IX was induced in the cancer cells, which was further supported by the fluorescence spectra of FIG. 5C.

Consequently, it was demonstrated that 5-aminolevulinic acid was encapsulated inside the nanocarrier of Example 1, and when cancer cells were treated with the nanocarrier, it was effectively delivered into the cells, leading to induction of protoporphyrin IX inside the cancer cells.

Experimental Example 5: Cytotoxicity Test of Nanocarrier

The nanocarrier obtained in Example 1 was subjected to a cytotoxicity test.

The C6 (rat glioma), A549 (human lung carcinoma), and MKN-74 (human gastric adenocarcinoma) cell lines cultured in Experimental Example 4 were used.

Additionally, 3T3-L1 (mouse fibroblast) cell line was also obtained from the Korea Cell Line Bank, and cultured in DEME (WELLGENE) supplemented with 1% penicillin-streptomycin (WELLGENE) and 10% bovine calf serum (BCS; WELLGENE) in an incubator at 37° C., 5% $CO_2$, and subculturing was performed every three days.

The four kinds of cell lines were subjected to cell counting kit (CCK)-8 assay.

In detail, each of the four kinds of cells ($5.0 \times 10^4$/mL) was seeded in each well of a 96-well plate, and then cultured for 24 hours. The medium was replaced by a serum-free medium, and then different concentrations (0.062 mg/mL, 0.125 mg/mL, 0.25 mg/mL, 0.5 mg/mL, 1 mg/mL, and 2 mg/mL) of the nanocarrier were added at a volume of 10% of the total volume. After incubation for 6 hours, 12 hours, and 24 hours, 10 μg of CCK-8 solution (CCK-8; Dojindo) was added thereto, followed by further incubation for 2 hours. Absorbance at 450 nm was measured using a microplate reader (iMark Bio-Rad instrumenis. Inc.). Absorbance was measured in triplicate under respective experimental conditions, and a mean value of the absorbance values was obtained, and compared with a mean value of absorbance values of a control group wherein a non-toxic phosphate buffer solution (PBS) was used instead of the nanocarrier to examine cytotoxicity.

The results are shown in FIGS. 6 to 9.

According to FIGS. 6 to 9, it was found that the nanocarrier according to an embodiment of the present disclosure showed no cytotoxicity against all the cancer cells, and also showed no cytotoxicity against normal cells.

Experimental Example 6: Evaluation of Cancer Cell Targetability of Hyaluronic Acid-Based Nanocarrier The C6 (rat glioma), A549 (human lung carcinoma), MKN-74 (human gastric adenocarcinoma), and 3T3-L1 (mouse fibroblast) cell lines cultured in Experimental Examples 4 and 5 were subjected to an uptake assay of the hyaluronic acid-based nanocarrier of Example 1 and the alginic acid-based nanocarrier of Comparative Example 1.

In detail, each of the four kinds of cells ($5.0 \times 10^5$/mL) was seeded in each well of a 24-well plate, and then cultured for 24 hours. The medium was replaced by a serum-free medium, and then 100 μL (1 mg/mL) of the nanocarrier corresponding to 10% of the total volume was added. After incubation for 1 hour, 3 hours, and 6 hours, cell fixation was performed. The medium in the well was completely aspirated, and then the well was washed with PBS three times. Cells were fixed in a 4% paraformaldehyde solution for 10 minutes, and then washed with PBS three times, and 4',6-diamidino-2-phenylindole (DAPI) staining was performed for cell nuclear staining. Cells were stained with IX DAPI for 3 minutes, and then washed with PBS three times. To prevent water from evaporating on the cell surface during microscopic observation, each well was covered with a cover glass. DAPI and PpIX fluorescence was examined using a fluorescence microscope (Carl Zeiss, Axiovert 200) under each condition.

The results are shown in FIGS. 10 to 13.

According to the results of FIGS. 10 to 13, the hyaluronic acid-based nanocarrier having cancer cell targetability according to an embodiment of the present disclosure showed PpIX fluorescence in all the cancer cells and no PpIX fluorescence in normal cells, whereas the alginic acid-based nanocarrier having no cancer cell targetability showed no PpIX fluorescence in all the cancer cells and normal cells. In contrast, DAPI fluorescence for nuclear staining was observed in all experimental groups, irrespective of the kind of the cancer cells and use of the hyaluronic acid-based nanocarrier.

As a result of fluorescence spectrum, no excitation and emission wavelengths were observed between a wavelength of 350 nm and a wavelength of 750 nm, and from the results of the hyaluronic acid-based nanocarrier, it was inferred that when the nanocarrier including 5-aminolevulinic acid is correctly internalized into cancer cells, protoporphyrin IX is induced. Absorbance and fluorescence spectrum results corresponding thereto were also obtained. Consequently, it was demonstrated that 5-aminolevulinic acid was encapsulated inside the nanocarrier according to an embodiment of the present disclosure, and 5-aminolevulinic acid was effectively delivered into cancer cells, leading to induction of protoporphyrin IX.

Experimental Example 7: Evaluation of Cancer Cell Targetability of Folic Acid-Alginic Acid-Based Nanocarrier A cell uptake assay of the nanocarrier obtained in Example 4 which was based on folic acid-alginic acid as a cancer cell-targeting ligand-binding polysaccharide was performed.

First, A549 (human lung carcinoma) and SK-OV-3 (human ovarian carcinoma) cell lines were obtained from the Korea Cell Line Bank (KCLB) and cultured in RPMI 1640 (WELLGENE) supplemented with 1% penicillin-streptomycin (WELLGENE) and 10% fetal bovine serum (FBS; WELLGENE) in an incubator at 37° C., 5% $CO_2$, and subculturing was performed every two days.

A cell uptake assay was performed in the same manner as in Experimental Example 6, except that cells were incubated for 3 hours after addition of the nanocarrier, followed by cell fixation. The results are shown in FIG. 14.

Figure 14:
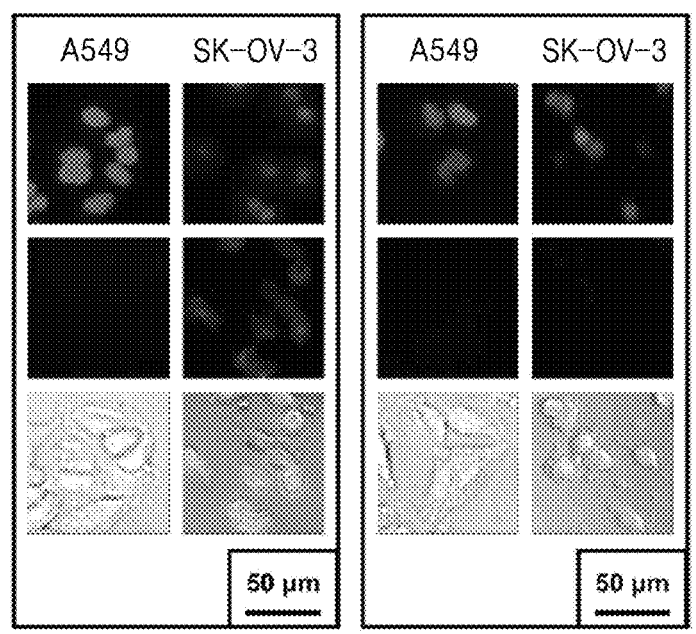
FIG. 14 shows fluorescence microscope images of DAPI and PpIX fluorescence which was observed after ovarian carcinoma cells and lung carcinoma cells were treated with each of a folic acid-alginic acid-based nanocarrier (FA-Alg-based carrier) of Example 4 and the alginic acid-based nanocarrier (Alg-based carrier) of Comparative Example 1 and left for a predetermined time.

According to the results of FIG. 14, the nanocarrier including the cancer cell-targeting ligand-binding polysaccharide according to an embodiment of the present disclosure showed PpIX fluorescence in the target ovarian carcinoma cell (SK-OV-3) and no PpIX fluorescence in the non-target lung carcinoma cell (A549). Further, the alginic acid-based nanocarrier of Comparative Example 1 having no cancer cell targetability showed no PpIX fluorescence in both the cells. In contrast, DAPI fluorescence for nuclear staining was observed in all experimental groups, irrespective of the kind of the cancer cells and use of the cancer cell-targeting ligand-binding polysaccharide-based nanocarrier.

Consequently, it was demonstrated that 5-aminolevulinic acid was encapsulated inside the cancer cell-targeting ligand-binding polysaccharide-based nanocarrier according to an embodiment of the present disclosure, and 5-aminolevulinic acid was selectively delivered into target cancer cells, leading to induction of protoporphyrin IX.

According to Experimental Examples 6 and 7, the nanocarriers according to the present disclosure may have cancer cell targetability and may exhibit PpIX fluorescence selectively for cancer cells, thereby being used in cancer diagnosis.

The present disclosure has been described with reference to preferred embodiments thereof. It will be understood by those skilled in the art to which the present disclosure pertains that the present disclosure may be implemented in a different specific form without changing the essential characteristics thereof. Therefore, it should be understood that the above embodiments are is not limitative, but illustrative in all aspects. The scope of the present disclosure is defined by the appended claims rather than by the foregoing description, and all differences within the scope of equivalents thereof should be construed as being included in the present disclosure.

The invention claimed is:

1. A micelle structured nanocarrier comprising an aqueous phase as an inner phase and comprising a surfactant on the surface thereof, wherein the micelle structured nanocarrier is obtained by dispersing a water-in-oil nanoemulsion comprising an oil phase ingredient, a surfactant, and an aqueous phase ingredient in water to remove the oil phase ingredient, wherein the aqueous phase comprises a cancer cell fluorescence-inducing substance and a cancer cell-targeting polysaccharide,
   wherein the cancer cell-targeting polysaccharide is entangled to each other to encapsulate the cancer cell fluorescence-inducing substance thereby forming an interpenetrating polymer network structure, wherein the cancer cell-targeting polysaccharide protrudes from a surface of the nanocarrier,
   wherein the micelle structured nanocarrier has an average size of 200 nm or less.

2. The nanocarrier of claim 1, wherein the aqueous phase ingredient comprises the cancer cell fluorescence-inducing substance and the cancer cell-targeting polysaccharide in a weight ratio of 1:1.

3. The nanocarrier of claim 1, wherein the nanocarrier has a zeta potential value of −10 mV to −30 mV or 10 mV to 30 mV.

4. The nanocarrier of claim 1, wherein the nanoemulsion comprises 70% by weight to 80% by weight of the oil phase ingredient, 10% by weight to 20% by weight of the aqueous phase ingredient, and 5% by weight to 15% by weight of the surfactant, based on the total weight of the nanoemulsion.

5. The nanocarrier of claim 1, wherein the surfactant is a single surfactant or a cosurfactant.

6. The nanocarrier of claim 1, wherein the surfactant is a cosurfactant having an HLB value of 6 to 9.

7. The nanocarrier of claim 1, wherein the surfactant is a mixture comprising sorbitan fatty acid ester and polyoxyethylene sorbitan fatty acid ester and having an HLB value of 6 to 9.

8. The nanocarrier of claim 1, wherein the cancer cell fluorescence-inducing substance is selected from the group consisting of heme, hemin, zinc protoporphyrin, magnesium protoporphyrin, hematoporphyrin, benzoporphyrin, metalloporphyrin, 5-aminolevulinic acid, texaphyrins, chlorins, purpurins, bacteriochlorins, phthalocyanine, naphthalocyanine, and any combination thereof.

9. The nanocarrier of claim 1, wherein the cancer cell-targeting polysaccharide is hyaluronic acid or a cancer cell-targeting ligand-binding polysaccharide.

10. The nanocarrier of claim 9, wherein the cancer cell-targeting polysaccharide is the cancer cell-targeting ligand-binding polysaccharide, and
    wherein the ligand of the cancer cell-targeting ligand-binding polysaccharide is selected from the group consisting of an aptamer, an antibody, a peptide, and a folic acid; and
    wherein the polysaccharide of the cancer cell-targeting ligand-binding polysaccharide is selected from the group consisting of alginic acid, chitosan, pectin, beta-glucan, cellulose, gelatin, hemicellulose, galactomannan, inulin, gum, and chitin.

11. The nanocarrier of claim 9, wherein the cancer cell-targeting polysaccharide is the cancer cell-targeting ligand-binding polysaccharide, and
    wherein the cancer cell-targeting ligand-binding polysaccharide is a folic acid-binding alginic acid.

12. The nanocarrier of claim 1, wherein the cancer cell fluorescence-inducing substance is 5-aminolevulinic acid, and the cancer cell-targeting polysaccharide is hyaluronic acid.

13. The nanocarrier of claim 1, wherein the oil phase ingredient is selected from the group consisting of soybean oil, olive oil, grape seed oil, canola oil, corn oil, mineral oil, silicone oil, castor oil, paraffin oil, and any combination thereof.

14. A method of contrasting cancer cells, the method comprising:
    administering an effective amount of the nanocarrier of claim 1 to a subject in need thereof.

15. The method of claim 14, wherein the cancer is selected from the group consisting of a brain tumor, lung cancer, stomach cancer, and ovarian cancer.

16. A method of preparing the nanocarrier of claim 1, the method comprising:
    preparing the oil phase ingredient;
    preparing the surfactant;
    preparing a first aqueous phase ingredient including the cancer cell-targeting polysaccharide;
    preparing a second aqueous phase ingredient including the cancer cell fluorescence-inducing substance;

preparing a water-in-oil nanoemulsion by mixing and stirring the oil phase ingredient, the surfactant, the first aqueous phase ingredient, and the second aqueous phase ingredient; and re-dispersing the water-in-oil nanoemulsion in water to remove the oil phase ingredient, thereby separating nanocarrier.

\* \* \* \* \*